United States Patent [19]

Cramm et al.

[11] 4,294,985
[45] Oct. 13, 1981

[54] PRODUCTION OF THIOCARBOHYDRAZIDE ON A COMMERCIAL SCALE

[75] Inventors: Günther Cramm, Cologne; Karl H. Blöcher, Leverkusen, both of Fed. Rep. of Germany

[73] Assignee: Bayer Aktiengesellschaft, Leverkusen, Fed. Rep. of Germany

[21] Appl. No.: 48,856

[22] Filed: Jun. 15, 1979

Related U.S. Application Data

[63] Continuation of Ser. No. 856,455, Nov. 30, 1977, abandoned.

[30] Foreign Application Priority Data

Dec. 23, 1976 [DE] Fed. Rep. of Germany ....... 2658557

[51] Int. Cl.$^3$ .......................................... C07C 159/00
[52] U.S. Cl. ...................................... 564/18; 260/704
[58] Field of Search ................. 260/552 SC, 704; 564/18

[56] References Cited

U.S. PATENT DOCUMENTS

| 2,657,234 | 10/1953 | Klarer et al. | 260/552 SC |
| 2,726,263 | 12/1955 | Audrieth et al. | 260/552 SC |
| 2,751,335 | 6/1956 | Carver et al. | 260/704 |
| 3,929,877 | 12/1975 | Toth et al. | 260/552 SC |
| 4,132,736 | 1/1979 | Cramm et al. | 260/552 SC |
| 4,172,092 | 10/1979 | Malone | 260/552 SC |

FOREIGN PATENT DOCUMENTS

| 83559 | 8/1971 | German Democratic Rep. | 260/552 SC |
| 754756 | 8/1956 | United Kingdom | 260/552 SC |

Primary Examiner—Arthur P. Demers
Attorney, Agent, or Firm—Sprung, Felfe, Horn, Lynch & Kramer

[57] ABSTRACT

In the production of thiocarbohydrazide by reacting hydrazine hydrate with carbon disulphide in the presence of water to form in a first stage hydrazinium dithiocarbazinate, subsequently thermally decomposing the hydrazinium dithiocarbazinate in a second stage to form thiocarbohydrazide, and recovering the thiocarbohydrazide from the reaction medium, the improvement which comprises effecting the entire reaction in the mother liquor of a preceding batch, carrying out the first reaction stage at a temperature between about 25° C. and 45° C., with injection of carbon disulphide below the surface of the reaction mixture; carrying out the second stage at about 62° to 65° C. without prior isolation of the intermediate product; filtering off the thiocarbohydrazide formed after cooling, separating the amount of mother liquor in excess of that required for the next batch, and feeding the balance of the mother liquor to the next batch. The excess mother liquor not required for the next batch is heated to about 70° to 75° C., and after separating off the thiocarbohydrazide, the remaining mother liquor is subjected to combustion.

3 Claims, No Drawings

PRODUCTION OF THIOCARBOHYDRAZIDE ON A COMMERCIAL SCALE

This is a continuation of application Ser. No. 856,455, filed Nov. 30, 1977, now abandoned.

The present invention relates to an unobvious process, which can be employed on a large industrial scale, for the preparation of thiocarbohydrazide starting from carbon disulphide and hydrazine hydrate.

Thiocarbohydrazide is used in large amounts as an intermediate for, inter alia, the preparation of agrochemicals, for example herbicides.

Numerous processes for the preparation of thiocarbohydrazide have already been disclosed (see the survey in Chem. Rev. 70, 111 et sec. (1970)). It is common to all the processes known hitherto that they only permit, with more or less success, a preparation of thiocarbohydrazide on a laboratory scale; on the other hand, the older processes previously known are virtually useless for obtaining thiocarbohydrazide on a large industrial scale.

U.S. Pat. No. 3,929,877 discloses a process for the preparation of thiocarbohydrazide. This process also uses carbon disulphide and hydrazine hydrate as the starting materials and surpasses all older processes known up to that time with respect to the yield of thiocarbohydrazide, relative to carbon disulphide (the yield relative to the economically more important hydrazine hydrate, however, cannot be ascertained). Provided adequate safety precautions are taken, the process is a good method for obtaining thiocarbohydrazide on a laboratory or pilot plant scale. On the other hand, the process also appears to be unsuitable for a procedure on a tonne scale, that is to say under large-scale industrial operating conditions.

The present invention now provides a process for the preparation of thiocarbohydrazide by reacting carbon disulphide with hydrazine hydrate in an aqueous phase containing hydrazine, with the formation of hydrazinium dithiocarbazinate, and by the subsequent thermal decomposition of the salt formed, in which the entire reaction is carried out in the mother liquor of a preceding batch, wherein the first stage is carried out at a temperature between about 25° and 45° C., with injection of carbon disulphide under the surface of the reaction mixture, which contains the total amount of hydrazine hydrate to be employed; the subsequent decomposition is carried out at a temperature between about 55° and 75° C., preferably at about 62° to 65° C., without prior isolation of the salt formed as the intermediate product; the reaction mixture is subsequently cooled to about 20°–25° C. and the thiocarbohydrazide formed is filtered off and washed with water; and the amount of mother liquor not required for the next batch is separated off and the bulk is fed to the next batch.

The mother liquor required for the first batch in accordance with the process according to the invention can be obtained by either (A) first of all effecting a reaction, in a manner known from the literature, in pure water (cf. Houben-Weyl, Methoden der organischen Chemie (Methods of Organic Chemistry), 4th Edition, Volume IX, page 909 (1955)), whereby a prolonged reaction time and an inferior yield must be accepted as disadvantages, or (B) making a "synthetic mother liquor", by adding, at the first batch, sulphur, ammonia, hydrogen sulphide and optionally ammonium polysulphides to aqueous hydrazine hydrate. Alternatively, one can start with water and then recycle through several cycles until a steady state is arrived at.

Because of the water content of the hydrazine hydrate, after the reaction of carbon disulphide with hydrazine hydrate an excess of mother liquor, and thus, if this excess is not completely worked up by special working-up processes, an effluent, is always obtained. In addition to the thiocarbohydrazide remaining in solution, the effluent contains, inter alia, small amounts of hydrazinium dithiocarbazinate and dimercaptothiadiazole, larger amounts of sulphur, hydrogen sulphide and ammonia and residues of excess hydrazine hydrate and is biologically degradable only to a very small degree.

A particular development of the process according to the invention is that combustion of this effluent, together with the wash waters, gives no residue so that in spite of the high nitrogen content no appreciable amounts of nitrous gases are formed and thus in the entire production process, in addition to the desired thiocarbohydrazide, only $H_2S$ and $SO_2$ are finally obtained, which can be converted by separate processes into elementary sulphur (see, for example, Application Ser. No. 689,876, filed May 25, 1976, now U.S. Pat. No. 4056606), or sodium sulphate (see, for example, application Ser. No. 783,368, filed Mar. 31, 1977, now abandoned.

The significant advantage of the process according to the invention is that, even when carried out on a large industrial scale, it can give yields of thiocarbohydrazide of over 86% of theory, the yield being relative to the economically more important component, hydrazine hydrate. These yields which can be achieved according to the invention are significantly higher than in the case of all previously known processes. A further advantage of the process can be seen in the fact that no special apparatus is required for carrying it out, but that it can be carried out in the apparatus customarily present in the chemical industry.

In detail, the process according to the invention generally takes the following form: the mother liquor from preceding batches and hydrazine hydrate are initially introduced into a reaction vessel, for example a kettle, and carbon disulphide is added. In order to avoid side-reactions, such as the formation of dimercaptothiadiazole, reaction temperatures which are as low as possible, from about 0° C. to a maximum of 25° C., are specified in the literature (see, for example, U.S. Pat. No. 3,929,877). With a heat of reaction of 35 Kcals/mol, this means a considerable expenditure on apparatus, on a large industrial scale, in order to remove the heat from the crystal sludge which forms. However, it has now been found that the reaction of hydrazine hydrate with carbon disulphide can be carried out at temperatures between 25° and 45° C., without having a disadvantageous effect on the course of the reaction or on the product composition, when the carbon disulphide is passed, in the finely divided state, into the reaction medium under slight pressure through immersed nozzles. At the same time, this procedure makes it possible, in a simple manner, for the waste air from the kettle to remain free from carbon disulphide, a circumstance which, with regard to the low ignition point of carbon disulphide, is of great importance for the further treatment of the waste air.

The method predominantly used according to the teaching of Examples 1-37 and 42 of U.S. Pat. No. 3,929,877 of isolating the hydrazinium dithiocarbazinate obtained as the intermediate product is possible on a large industrial scale only with considerable expenditure since this salt is not very stable to heat (sec, for example, Naturforsch, 16 b, 769 (1961); Chem. Rev. 70 (1) page 114, lefthand column, 2nd paragraph (1970) and Houben-Weyl, Methoden der organischen Chemie (Methods of Organic Chemistry), 4th edition, volume IX, page 909 (1955)and can easily decompose with the formation of highly toxic substances such as hydrogen sullphide. Thus, for reasons of safety this method should be avoided on a large industrial scale.

Isolation of the intermediate product is therefore dispensed with in the process according to the invention. Instead, after the addition of carbon disulphide has ended, the contents of the kettle are either warmed directly to the reaction temperature of 55°–75° C. used for the formation of the thiocarbohydrazide, preferably to 62°–65° C., or are first introduced into another kettle which, in contrast to the 1st batch kettle, can be in a section of the production installation not provided with as much and as costly explosion-proof protection, where the reaction to give the thiocarbohydrazide is then carried out at the above-mentioned temperature.

At the preferred temperature of about 62°–65° C. the reaction time is about 10–12 hours. It is thus indeed longer than in the case of processes described hitherto, which all use higher reaction temperatures, but this is no disadvantage from the economic point of view. Parallel to the formation of thiocarbohydrazide, some of the hydrazine hydrate decomposes, inter alia with the formation of ammonia and nitrogen. This reaction can lead to considerable losses of hydrazine hydrate, in particular at higher temperatures, and is probably one of the reasons that the yield of the processes known hitherto is considerably lower, relative to hydrazine hydrate, than the yields, of over 86% of theory, that can be achieved according to the invention.

In addition, the evolution of gas can become very violent and uncontrolled, especially at higher temperatures, and thus when the reaction is carried out in a factory, considerably larger absorption installations are required at a temperature of 70° C. than are necessary at the preferred reaction temperature of 62°–65° C.

The use of a mother liquor as a reaction medium is indeed not new but is frequently a proven means, for example, of avoiding losses caused by solubility, or of not having to bring reactions to completion. However, in addition to these customary advantages, under the reaction conditions preferred according to the invention the mother liquor surprisingly has an extremely favorable "catalytic effect" on the thermal decomposition of the hydrazinium dithiocarbazinate, which manifests itself, in particular, in a shorter reaction time, lower formation of by-products and thus, finally, in a higher yield. This becomes particularly evident when the reaction in pure water under otherwise identical conditions, such as has previously been described in the literature (see Houben-Weyl, Methoden der organischen Chemie (Methods of Organic Chemistry), 4th edition, volume IX, page 909 (1955)), is used for comparison.

The mother liquor is also used for the second reaction step according to the process described in Example 42 of U.S. Pat. No. 3,929,877; however, in order to achieve a good yield, hydrogen sulphide must first be added to the mother liquor, a measure which requires additional industrial installations and which is not necessary in the procedure according to the invention.

According to Examples 1 to 41 of U.S. Pat. No. 3,929,877 the reaction product is predominantly isolated by distilling off the reaction medium under reduced pressure. This may be readily carried out on a laboratory scale, but it is unsuitable for a factory scale, and in addition the reaction product must be subsequently recrystallized, which again reduces the practicality of the process. On the other hand, by the process according to the invention, after the reaction has ended, at a degree of conversion of 94–97%, the contents of the kettle are merely cooled to 20°–25° C. Sufficiently pure thiocarbohydrazide is then isolated by filtration on a stirred pressure filter or on a centrifuge. The bulk of the mother liquor obtained is used again for the next batch and the other portion is fed to the working up process.

In working up the excess mother liquor, the thermal decomposition is first brought to completion by heating the mother liquor to about 73°–75° C. for about 2–3 hours, the thiocarbohydrazide which precipitates after cooling is separated off and the mother liquor and wash waters which then remain are subjected to combustion. In addition to the after-treatment, with heat, of the excess mother liquor and subsequent combustion, it is also possible to strip off about 75–90% of the water, which is incorporated into the reaction by hydrazine hydrate, from some of the mother liquor by gentle distillation under reduced pressure.

Thus, in contrast to the teaching in U.S. Pat. No. 3,929,877, the water is distilled off but as far as possible no hydrazine hydrate; instead the latter is left in the distillation sump and this, after filtering off any sulphur which may precipitate, is mixed with non-treated original mother liquor and is used directly for the next feed. The residue of mother liquor still remaining is then either after-treated with heat or subjected to combustion directly; the amount of thiocarbohydrazide to be produced, that is to say finally the practicality of the entire process, is the determining factor for this.

The hydrazine hydrate used is preferably the 100% pure material, but products which are more dilute, for example about 80–85% strength, that is to say which contain more water, can also be employed. This is of minor importance for the actual reaction; however, a higher water content increases the load on the working-up of the excess of mother liquor, more of which is then obtained.

A particular characteristic of the combustion is that the effluent is not passed centrally through the flame, as is otherwise customary, but is injected at right angles to the main flame. In this manner, the combustion of the effluents of the present process can take place without giving a residue and without appreciable amounts of nitrous gases forming, in spite of the high nitrogen content.

The process of the present invention is illustrated by the following preparative examples:

EXAMPLE 1

6,300 l of mother liquor (such as produced in Example 6 of Application Ser. No. 641,705, filed Dec. 17, 1975 now pending) and 5,00 l of hydrazine hydrate were initially introduced in a 16 m³ stirred kettle and 2,750 l of carbon disulphide were injected near the bottom with a pumppressure of 3 to 4 bars and at a temperature of at most 43° C., with the aid of a pump in the course of 10 hours. The contents of the kettle were then warmed to 62°–64° C. and kept at this temperature for 10–12 hours; the thiocarbohydrazide (TCH) which precipitated after cooling to 20°-25° C. was separated off on a stirred pressure filter or in a centrifuge and washed with water. 4,420 kg of TCH were obtained.

6,300 l of the 8,000 l of mother liquor were used for the next batch; the excess of 1,700 l was collected and worked up.

The hydrogen sulphide liberated during the formation of the TCH was first washed with dilute sulphuric acid and then fixed in a sodium hydroxide solution as NaHS.

The excesses of mother liquor from each of three batches, a total of 5,100 l, were heated together to 73°-75° C. for 2½ hours. After cooling, a further 780 kg of TCH were isolated, so that an average of 4,680 kg of TCH were obtained per batch, which corresponded to a yield of 96.3% of theory, relative to $CS_2$, or 86.1% of theory, relative to hydrazine hydrate.

The mother liquor obtained after the after-treatment with heat was subjected to combustion, together with the wash waters.

EXAMPLE 2

As described in Example 1, the same amounts of hydrazine hydrate and carbon disulphide were reacted to give thiocarbohydrazide. From 4,000 l of 8,000 l of mother liquor obtained, 1,500 l of water were distilled off under reduced pressure at 45°-55° C. without appreciable amounts of hydrazine hydrate being entrained. The warm distillation sump was filtered in order to separate off any sulphur which may have precipitated and was made up to 6,300 l with non-treated mother liquor and used again as the reaction medium for the next charge.

The excess mother liquor was collected and after-treated with heat as described in Example 1 and, after filtering off the TCH, was subjected to combustion, together with the wash waters.

The yield of TCH was 4,760 kg, which corresponded to a yield of 97.9% of theory, relative to $CS_2$, or 87.6% of theory, relative to hydrazine hydrate.

It will be appreciated that the instant specification and examples are set forth by way of illustration and not limitation, and that various modifications and changes may be made without departing from the spirit and scope of the present invention.

What is claimed is:

1. In the production of thiocarbohydrazide by reacting hydrazine hydrate with carbon disulphide in the presence of water to form in a first stage hydrazinium dithiocarbazinate, subsequently thermally decomposing the hydrazinium dithiocarbazinate in a second stage to form thiocarbohydrazide, and recovering the thiocarbohydrazide from the reaction medium, the improvement which comprises effecting the entire reaction in the mother liquor of a preceding batch, carrying out the first reaction stage at a temperature between about 25° C. and 45° C., with injection of carbon disulphide below the surface of the reaction mixture carrying out the second stage at about 62° to 65° C. without prior isolation of the intermediate product; subsequently cooling the reaction mixture to about 20° to 25° C. and filtering off the thiocarbohydrazide formed, separating the amount of mother liquor in excess of that required for the next batch, and feeding the balance of the mother liquor to the next batch.

2. A process according to claim 1, including the further steps of heating the excess mother liquor not required for the next batch to about 70° to 75° C., separating off the thiocarbohydrazide, after cooling and subjecting the remaining mother liquor to combustion.

3. A process according to claim 1, in which about 75 to 90% of the water introduced into the process by the hydrazine hydrate is distilled off under reduced pressure at about 45° to 60° C. from a portion of the mother liquor, the concentrated mother liquor being fed to the next batch together with non-treated mother liquor, whereby the thiocarbohydrazide is obtained in a yield of at least about 86% based on hydrazine.

* * * * *